United States Patent [19]

Occelli et al.

[11] Patent Number: 4,783,461

[45] Date of Patent: Nov. 8, 1988

[54] 3,6-DISUBSTITUTED TRIAZOLO [3,4-A]PHTHALAZINE DERIVATIVES

[75] Inventors: Emilio Occelli, Parabiago; Giorgio Tarzia, Milan, both of Italy

[73] Assignee: Gruppo Lepetit S.p.A., Gerenzano, Italy

[21] Appl. No.: 629,658

[22] Filed: Jul. 11, 1984

[30] Foreign Application Priority Data

Jul. 12, 1983 [IT] Italy ................ 22014 A/83

[51] Int. Cl.$^4$ ............ A61K 31/50; A61K 31/55; C07D 487/04
[52] U.S. Cl. .................. 514/248; 544/234; 544/115; 514/212; 514/218; 514/233.2; 540/553; 540/575; 540/599
[58] Field of Search ............ 514/253, 248, 212, 218, 514/227; 544/234, 115; 540/553, 575, 599

[56] References Cited

U.S. PATENT DOCUMENTS

| | | | |
|---|---|---|---|
| 2,484,029 | 10/1949 | Hartmann et al. | 544/237 |
| 3,694,442 | 9/1972 | Houlihan | 544/234 |
| 3,704,300 | 11/1972 | Hardtmann | 544/234 |
| 3,711,481 | 1/1973 | Hardtmann | 544/234 |
| 4,391,807 | 7/1983 | Alexander et al. | 544/234 |
| 4,485,106 | 11/1984 | Peet et al. | 544/234 |
| 4,487,930 | 12/1984 | Peet et al. | 544/234 |

FOREIGN PATENT DOCUMENTS

| | | |
|---|---|---|
| 29130 | 5/1981 | European Pat. Off. |
| 0085840 | 8/1983 | European Pat. Off. |
| 53-21197 | 2/1978 | Japan |
| 629177 | 12/1946 | United Kingdom |

OTHER PUBLICATIONS

G. A. Reynolds, et al., J. Org. Chem., 24, 1205 (1959).
H. Zimmer, et al., J. Org. Chem., 40, 2901 (1975).
K. Ueno, et al., Chemical and Pharmaceutical Bulletin, 24(5), 1068 (1976).
Chemical Abstract Number 92:94311b abstracting D. Twomey, Proc. R. Ir. Acad., Sect. B 79B(3), 29 (1979).
Potts et al., J. Org. Chem., vol. 34, No. 11, pp. 3221-3230, 1969.
Buzykin et al., Chemical Abstracts, vol. 89:146857u, 1978.
Twomey, Chemical Abstracts, vol. 81; 3864t, 1974.
Badr et al., J. Het. Chem., vol. 21, pp. 471-475, (1984).
Druey et al., Fasciculus I, vol. 34, No. 21, pp. 195-210, (1951).
Moroi et al, Chem. Pharm. Bull., vol. 24, No. 11, pp. 2850-2856, (1976).
Twomey, Proc. Roy. Irish Acad. Science, vol. 74B, pp. 37-52 (1976).

Primary Examiner—Donald G. Daus
Assistant Examiner—William A. Teoli, Jr.
Attorney, Agent, or Firm—Stephen L. Nesbitt

[57] ABSTRACT

The present invention is directed to new 3,6-disubstituted-1,2,4-triazolo[3,4-a]phthalazine derivatives of formula I

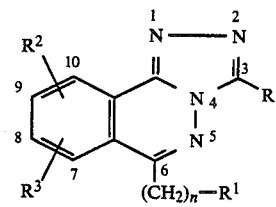

wherein R represents phenyl or substituted phenyl, n is 1 or 2, $R^1$ is an amino group of formula $NR^4R^5$, or an alkoxy of cycloalkoxy group of formula $OR^6$, and $R^2$ and $R^3$ represent hydrogen, halogen, $(C_1-C_4)$alkyl or $(C_1-C_4)$alkoxy, to the process for their preparation and to the pharmaceutical compositions containing them. The compounds of the present invention are as active as anti-anxiety substances.

7 Claims, No Drawings

3,6-DISUBSTITUTED TRIAZOLO [3,4-A]PHTHALAZINE DERIVATIVES

The present invention is directed to new 3,6-disubstituted-1,2,4-triazolo[3,4-a]phthalazine derivatives, to the process for their preparation and to the pharmaceutical compositions containing them.

The new 1,2,4-triazolo[3,4-a]phthalazines of the present invention are represented by the following formula

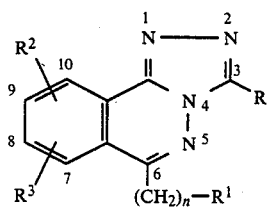

wherein
R represents phenyl or substituted phenyl wherein the phenyl ring is substituted with one, two or three substituents independently selected from $(C_1-C_4)$alkyl, $(C_1-C_4)$alkoxy, halogen, phenyl, hydroxy, amino, mono- and di-$(C_1-C_4)$alkylamino, $(C_2-C_4)$alkanoylamino and trifluoromethyl;
n is 1 or 2;
$R^1$ is selected from an amino group of formula $NR^4R^5$ wherein $R^4$ and $R^5$, each independently, represents hydrogen, $(C_1-C_4)$alkyl, $(C_2-C_4)$alkenyl, $(C_1-C_4)$alkyl substituted with one or two groups independently selected from hydroxy, $(C_1-C_4)$alkoxy, halogen, carboxy and $(C_1-C_4)$alkoxycarbonyl; a $(C_1-C_4)$alkyl or substituted phenyl-$(C_1-C_4)$alkyl group wherein the alkyl portion may be substituted as defined above and the phenyl portion may be substituted with 1, 2 or 3 substituents selected from $(C_1-C_4)$alkyl, $(C_1-C_4)$alkoxy, halogen, phenyl, hydroxy, amino, mono- and di-$(C_1-C_4)$alkylamino, $(C_1-C_4)$alkanoylamino, and trifluoromethyl, or $R^4$ and $R^5$ taken together with the adjacent nitrogen atom may represent a saturated 4, 5, 6 or 7-membered heterocyclic ring which may contain a further heteroatom selected from nitrogen, oxygen and sulfur and optionally bear one or two substituents independently selected from $(C_1-C_4)$alkyl, phenyl, substituted phenyl, hydroxy, and carbo-$(C_1-C_4)$alkoxy, or $R^1$ represents an alkoxy or cycloalkoxy group of formula —$OR^6$ wherein $R^6$ stands for a $(C_1-C_6)$alkyl group substituted with one or two groups independently selected from hydroxy, amino, mono- or di-$(C_1-C_4)$alkylamino, $(C_1-C_4)$alkoxy, halogen, oxo, carboxy, and $(C_1-C_4)$alkoxycarbonyl, or $R^6$ is a $(C_5-C_8)$cycloalkyl group optionally substituted with one or more hydroxy or $(C_1-C_4)$alkoxy groups and
$R^2$ and $R^3$, each independently, represents hydrogen, halogen, $(C_1-C_4)$alkyl or $(C_1-C_4)$alkoxy.

Since some of the compounds of the invention possess basic functions (e.g. amines) capable of forming acid-addition salts, the present invention also encompasses the pharmaceutically-acceptable acid-addition salts of these compounds.

As used herein the term "substituted phenyl" is intended to refer to a phenyl group wherein one, two or three hydrogens are replaced by groups each independently selected from $(C_1-C_4)$alkyl, $(C_1-C_4)$alkoxy, halogen, phenyl, hydroxy, amino, mono- and di-$(C_1-C_4)$alkylamino, $(C_2-C_4)$alkanoylamino and trifluoromethyl.

The terms "alkyl" or "alkoxy" per se, as well as the alkyl or alkoxy portions in other substituents containing said moieties, designate straight or branched alkyl or alkoxy groups which contain a number of carbon atoms within the range specified between parenthesis. Thus, for instance, the term "$(C_1-C_4)$alkyl" designates a straight or branched alkyl radical which may contain 1, 2, 3 or 4 carbon atoms.

The term "halogen" identifies chlorine, bromine, fluorine and iodine atoms.

Representative examples of "saturated 4, 5, 6 or 7 membered heterocyclic rings" as defined in the present invention are: oxazolidinyl isoxazolidinyl, azetidinyl, pyrrolidinyl, piperidinyl, pyrazolidinyl, pyrazinidyl, pyrimidinyl pyridazinidyl, morpholinyl, imidazolidinyl, piperazinyl, triazolidinyl, perhydroazepinyl, perhydrodiazepinyl and the like.

"Pharmaceutically-acceptable acid-addition salts" are the acid addition salts of the compounds of formula I which are not toxic, i.e. whose anion is relatively harmless at dosages compatible with good antianxiety activity in animals so that the pharmacological effects of the compounds of the invention are not impaired by possible side-effects of the anion.

Representative examples of pharmaceutically-acceptable acid-addition salts are the acid-addition salts of the selected compounds of formula I with mineral acids such as hydrochloric, hydrobromic, sulfuric and phosphoric acid, or with organic, carboxylic or sulfonic acids, such as lactic, succinic, oxalic, citric, tartaric, p.toluenesulfonic, benzenesulfonic, methanesulfonic and the like.

A preferred group of compounds of the invention includes those compounds of formula I wherein R is phenyl or substituted phenyl, and $R^1$ is an amine of formula $NR^4R^5$, wherein $R^4$ and $R^5$ are as defined above.

A further group of preferred compounds includes those compounds of formula I wherein R is phenyl and $R^1$ is $NR^4R^5$ wherein $R^4$ and $R^5$ represent $(C_1-C_4)$alkyl groups or $(C_1-C_4)$alkyl groups substituted as defined above or $R^4$ and $R^5$ taken together with the adjacent nitrogen atom represent a pyrrolidino, pyrazolidino, piperidino, imidazolidino and morpholino group.

The compounds of the present invention when tested in vitro in the benzodiazepine receptor binding test, showed to act selectively on the rat brain benzodiazepine receptors displacing $^3$H-diazepam from its specific receptors with a considerable potency. Furthermore, the compounds of the present invention showed to be able to displace $^3$-H-diazepam from its specific brain receptors also when tested in vivo.

This activity in benzodiazepine receptors is known to reflect, and actually reflects, an antianxiety activity which is detectable in animals by the pharmacological tests usually employed in this field. Said activity is of particular interest in that at the effective doses tested, it is not accompanied by the side effects typically associated to benzodiazepines, such as sedation, motor incoordination, etc.

The s-triazolo[3,4-a]phthalazine ring system was first reported in literature in 1951 when J. Druey and B. H.

Ringier in Helvetica Chimica Acta 34, 195, described the synthesis and the physico-chemical characteristics of a series of s-triazolo[3,4-a]phthalazines.

Since then, the study of this new ring system developed considerably, leading to the synthesis of several other s-triazolo[3,4-a]phthalazine derivatives, with interest being directed essentially toward their antihypertensive properties (see for instance Chem. Abstracts 80, 37056 a, (1974) and Dissertation Abstr. Intern. B 32, No. 7, 3859 (1972)). This study was further stimulated by the identification of metabolites of hydralazine and budralazine having a triazolo-phthalazine structure (see Arzneimittel-Forsch., 1977, II, 27, 2388-95; Chem. Pharm. Bull. 22, No. 12, 3006–09 (1974) and Chem. Pharm. Bull. 24, No. 11, 2850–58 (1976)). Furthermore several other triazolo[3,4-a]phthalazines have been synthesized up to now, having a different pharmacological activity such as the antiinflammatory activity (see for instance Japanese Patent Application No. 104949/74, Kokai No. 51/032598 (Derwent: Farmdoc 33086 X)), the anticancer activity (see Chem. Abstr. 81, 3864 t, 1974) and the bronchodilating activity (see Chem. Abstr. 80, 37073 d, 1974)). Other s-triazolo[3,4-a]phthalazines are disclosed in Chem. Abstr. 89, 146857n, 1978.

A general method for preparing the compounds of the invention is a multistep procedure which comprises the alcoholysis of a cyano-triazolo-phthalazine of the following formula II

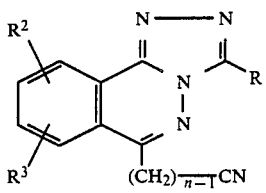
II wherein R, $R^2$ and $R^3$ are as defined above, to give the corresponding lower alkyl ester of formula III

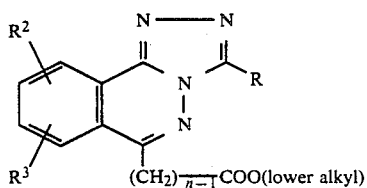
III which in turn reduced to the corresponding alcohol derivative of formula IV

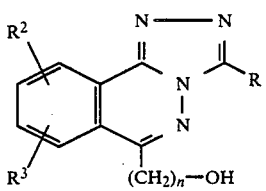
IV

The alcoholic function of the triazolo-phthalazine derivative of formula IV is then substituted with a "good leaving group" function, such as a halogen atom or an ester-reactive function to give a triazolo-phthalazine derivative of formula V

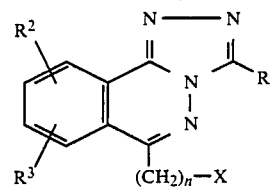
V wherein X is a "good leaving group" as above defined.

Examples of "ester-reactive functions" which can be used in this reaction step are sulfonic esters such as the mesylate, tosylate and the like.

These "ester-reactive functions" are especially preferred when the substrate of the reaction is a 1,2,4-triazolo-phthalazine of the above formula wherein n is equal to 2.

Finally, the above 1,2,4-triazolo-phthalazine of formula V is reacted with an amine or formula $HNR^4R^5$, wherein $R^4$ and $R^5$ are as above defined, or with an alkoxide or cycloalkoxide of formula $MeOR^6$ wherein $R^6$ is as above defined and Me represents an alkali metal atom, to give the desired 1,2,4-triazolo-phthalazine of formula I. More particularly, the alcoholysis of the cyano-triazolo-phthalazine of formula II is conducted by treating a mixture of the compound of formula II in a lower alkanol with hydrogen chloride and hydrolyzing the iminoester hydrochloride so obtained to give the corresponding carboxylic ester, which is recovered by filtration and purified, if necessary or desired, by crystallization.

The subsequent reduction of the ester derivative of formula III employs an alkali metal boron hydride, such as NaBH, or LiBH, which are usually used in reducing an ester function to an alcohol one. Alternatively, other reducing agents such as $LiAlH$, $AlH_3$, $LiAlH(OCH_3)_3$ or $NaBH(OCH_3)_3$ can be used.

This reaction is carried out in the presence of a suitable polar aprotic inert organic solvent.

Preferably the reaction is conducted at the reflux temperature for some hours, and the reaction course is monitored by means of TLC.

The hydroxy intermediate of formula IV is then recovered by means of known per se techniques which includes removing the excess reducing agent, evaporating the solvent under reduced pressure, washing the crude residue with water and drying it. The obtained crude intermediate compound of formula IV can be used as such in the subsequent reaction step. However, it may be purified according to usual techniques, such as crystallization.

The next reaction step, the introduction of the "good leaving group" —X, is conducted by known per se techniques which include, when X is a chlorine, bromine or iodine atom, reacting the hydroxy intermediate of formula IV with the suitable hydrohalidic acid, or preferably, with a suitable halogenating agent which is an inorganic acid halogenide, e.g. $SOCl_2$, $PCl_5$, $PCl_3$, $POCl_3$ and the like, and when X is a sulfonic acid functional group, reacting the intermediate of formula IV with a sulfonic acid activated derivative, preferably a sulfonic acid halogenide.

The reaction is conducted in the presence of an aprotic inert organic solvent such as a halogenated aliphatic hydrocarbon, (e.g. methylene chloride) and chloroform; tetrahydrofuran; an aromatic hydrocarbon (e.g. benzene, toluene or xylene).

When preparing sulfonic acid esters of formula V, it is preferred to conduct the reaction in the presence of a hydrohalidic acid acceptor, preferably a base but more preferably an organic tertiary amine such as a trialkylamine, pyridine, collidine, picoline and the like.

When a compound of formula I is obtained wherein $R^1$ is $NR^4R^5$ *and at least one of $R^4$* and $R^5$ is a hydroxy($C_1$-$C_4$)alkyl group, it may be transformed into the corresponding halogen($C_1$-$C_4$)alkyl by means of known per se halogenation techniques. These halo($C_1$-$C_4$)alkyl derivatives of formula I, and preferably the chloro($C_1$-$C_4$)alkyl ones, can in turn be reacted with an alkali metal alkoxide to give the corresponding derivatives of formula I wherein $R^4$ and/or $R^5$ represent a ($C_1$-$C_4$)alkoxy($C_1$-$C_4$)alkyl group.

Alternatively, the triazolo-pthalazine derivatives of formula I wherein $R^1$ represents the group $OR^6$ can be prepared by reacting the alcohol intermediate of formula IV with an alkali metal hydride to give the corresponding alkali metal alkoxide whch is then reacted with a compound of formula Y—$R^6$ wherein $R^6$ is as above and Y represents chloro, bromo or iodo, to give the desired product of formula I.

The nitrile derivatives of formula II can be prepared according to the usual procedures, either by reacting the corresponding haloalkyl or sulfonic ester-triazolophthalazine with an alkali metal or copper cyanide or by reacting a 1-phthalazino-hydrazine bearing a group of formula $(CH_2)_{n-1}$—CN in position 4, with the selected benzoylchloride of formula RCOCl, (wherein R is as defined above).

The pharmacological properties of the compounds of the present invention were first investigated by submitting some representative members of this class to the benzodiazepine-receptor binding-test in vitro. In this test, which was carried out by following essentially the method described in H. Möhler and T. Okada in Life Sciences, Vol. 20, 2101–2110 (1977), the affinity of the test compounds for the $^3$H-diazepam receptor was quantitatively estimated by measuring the inhibition of specific $^3$H-diazepam binding to rat brain membranes by the test compounds.

The inhibition is expressed in term of inhibition constant $K_i$ which is defined as $K_i = IC_{50}/(1+C/K_D)$ wherein $IC_{50}$ is the concentration of test substance required to displace 50 percent of the specific $^3$H-diazepam binding, C is $^3$H-diazepam concentration and $K_D$ is the affinity constant of $^3$H-diazepam for its receptor ($3.4 \times 10^{-9}$M). Compounds with high affinity for the receptor will displace $^3$H-diazepam at low concentrations (low $IC_{50}$ values) and are therefore characterized by a low $K_i$. For instance, in this test the compounds of Examples 1 and 2 exhibited a $K_i$ value of $2 \times 10^{-8}$ and $1.5 \times 10^{-7}$, respectively.

The ability of the compounds of the present invention to increase punished responding in animals in a conflict situation, a procedure with high validity for predicting the anxiolytic effect of drugs, was assessed by testing these compounds in rats according to the method described by J. R. Vogel, B. Beer, E. D. Clody in Psychopharmacologia 21, 1–7 (1971) as modified by A. S. Lippa et al., in "Anxiolytics, Industrial Pharmacology", Vol. 3, Futura Publishing, 1979, pages 41–81. Briefly, rats are deprived for water for 48 hours and deprived of food for 20 hours prior to testing. Sixty minutes after administration of the test compound each rat is placed in an especially equipped cage. A glucose solution is available from a tap located in the rear of the cage. A constant pulsating shocking current is connected between the grid floor and the tap. Each rat is allowed 20 seconds of non-shocked drinking, then cycles of 5 seconds shock-off and 5 seconds shock-on began. During the shock-on period each lick on the tap is accompanied by shock. The number of shocks received by each animal is recorded and minimal effective doses are determined.

The minimal effective dose (MED) is the minimal dose which significantly increases the number of shocks in the treated animals in comparison with controls.

The MED of the compound of Example 1 in this test is 5 mg/kg, i.p.

With the term "use" it is intended to refer to all industrially applicable aspects and acts of said use, including the embodiments of the novel compounds into pharmaceutical compositions.

Suitable pharmaceutical compositions contain the novel compounds in admixture or conjunction with organic or inorganic, solid or liquid pharmaceutical excipients and may be employed for enteral or parenteral administration. Suitable excipients are substances that do not react with the new compounds, such as for instance, water, gelatin, lactose, starches, magnesium stearate, talcum, vegetable oil, benzyl alcohol, polyalkyleneglycols or other known medicinal excipients. The new compounds may be administered by various routes: while the preferred route of administration is the oral one, intramuscular or intravenous administration can also be employed. For oral administration, the substances are compounded in forms such as tablets, dispersible powders, capsules, granules, syrups, elixirs and solutions. For intraveneous or intrasmuscular administration the active ingredients are embodied into injectable dosage forms.

Such compositions are formulated as known in the art. The dosage regimen for the compounds of the present invention to be used in an anti-anxiety treatment will depend upon a variety of factors including the particular compound used, the route of administration, and the type of treatment applied for. Good results can be obtained, however, by administering the compounds of the present invention at a daily dosage range comprised between about 0.1 and about 2.0 preferably administered in divided doses. It is however clear that a daily dosage beyond the above indicated range may also be employed depending on the individual conditions of the subject to be treated. Accordingly, the present invention provides a therapeutic composition comprising from about 25 to about 250 mg of one of the compounds of the invention as the active ingredient together with a pharmaceutically acceptable carrier.

As an example, the active compounds of formula I can be formulated as in the following:

A capsule is prepared with

| | |
|---|---|
| 6-[(2-methoxyethoxy)methyl]-3-(4-methoxyphenyl)-1,2,4-triazolo-[3,4-a]phthalazine | 200 mg |
| Saccharose | 35 mg |
| Polyvinylpyrrolidone | 5 mg |
| Sodium dioctylsulfosuccinate | 1.8 mg |
| Magnesium stearate | 10 mg |
| Corn starch | q.s. to 300 mg |

A tablet is prepared with

| | |
|---|---|
| 6-[(2-methoxyethoxy)methyl]-3-(4-methoxyphenyl)-1,2,4-triazolo-[3,4-a]phthalazine | 150 mg |
| Saccharose | 30 mg |
| Polyvinylpyrrolidone | 5 mg |
| Sodium dioctylsulfosuccinate | 1.4 mg |
| Magnesium stearate | 8 mg |
| Corn starch | q.s. to 250 mg |

The following examples describe the preparation of some representative compounds of the invention.

Since the exemplified methods are generally applicable simply by selecting the proper substrates according to the suggestions of the present disclosure, the following examples cannot be construed as limiting the scope of the present invention.

EXAMPLE 1

6-[(2-Methoxyethoxy)methyl]-3-(4-methoxyphenyl)-1,2,4-triazolo[3,4-a]phthalazine (A) 3-(4-methoxyphenyl)-1,2,4-triazolo[3,4-a]-phthalazin-6-carbonitrile (26 g) is suspended in cold anhydrous ethanol (550 ml), the cooled mixture is saturated with hydrogen chloride, slowly heated to reflux and kept at the reflux temperature for 2 h. Then, about 200 ml of ethanol are distilled off under reduced pressure and replaced with fresh anhydrous ethanol. The mixture is heated to reflux and kept at this temperature for about 14–16 h under slow hydrogen chloride stream. The solvent is then evaporated under reduced pressure, the residue is taken up with ice-water (200 ml) and the pH of the mixture is adjusted to about 7.5 by adding sodium bicarbonate. After stirring for a few minutes, the reaction mixture is filtered and the collected solid is crystallized from ethanol/chloroform yielding 3-(4-methoxyphenyl)-1,2,4-triazolo[3,4-a]phthalazin-6-carboxylic acid ethyl ester (27 g). M.p. 180°–182° C.

(B) NaBH$_4$ (3.8 g, 0.1 mol) is dissolved in recently distilled diglyme (120 ml) under anhydrous conditions. Anhydrous LiBr (8.7 g, 0.1 mol) is added and the mixture is stirred for 30 min at room temperature. The ester derivative obtained in the foregoing step A (23 g, 0.066 mol) in diglyme (50 ml) is added portionwise. This mixture is then heated to about 80° C. for 10 h, then it is cooled, poured into water (800 ml) and the pH of the resulting mixture is brought to about 7 with acetic acid. After stirring for about 20 min, the mixture is filtered and the recovered solid is crystallized from ethanol/chloroform yielding 11.1 g of 3-(4-methoxyphenyl)-1,2,4-triazolo[3,4-a]phthalazin-6-methanol. M.p. 225°–227° C.

(C) A portion of the above obtained 3-(4-methoxyphenyl)-1,2,4-triazolo[3,4-a]phthalazin-6-methanol (10.8 g), anhydrous chloroform (100 ml) and a drop of dimethylformamide are heated at reflux for 6 h, then the solvent is evaporated, the residue is disaggregated with diluted aqueous sodium bicarbonate and filtered. The collected solid is crystallized from ethanol/chloroform yielding 6-(chloromethyl)-3-(4-methoxyphenyl)-1,2,4-triazolo[3,4-a]phthalazine (10.3 g). M.p. 203°–206° C.

(D) Sodium (0.4 g) is dissolved in anhydrous methylcellosolve (60 ml) with stirring and then a portion of 4.5 g of 6-(chloromethyl)-3-(4-methoxyphenyl)-1,2,4-triazolo[3,4-a]phthalazine as obtained above is rapidly added. The mixture is heated at about 120° C. for about 5 h, the solvent is evaporated off under reduced pressure, the residue is washed with a small amount of water and crystallized from methanol/water yielding 6-[(2-methoxyethoxy)methyl]-3-(4-methoxyphenyl)-1,2,4-triazolo[3,4-a]phthalazine (3 g). M.P. 129°–131° C.

N.M.R. and I.R. spectra are in agreement with the assigned structure.

EXAMPLE 2

3-(4-Methoxyphenyl)-6-[(1-pyrrolidinyl)methyl]-1,2,4-triazolo[3,4-a]phthalazine 6-(Chloromethyl)-3-(4-methoxyphenyl)-1,2,4-triazolo[3,4-a]phthalazine (3 g) and pyrrolidine (30 ml) are heated at 100° C. for 8 h in autoclave. The amine excess is removed, the residue is washed with a small amount of water and crystallized from ethyl acetate, yielding 3-(4-methoxyphenyl)-6-[1-pyrrolidinyl)methyl]-1,2,4-triazolo[3,4-a]phthalazine (1.7 g). M.p. 184°–186° C.

EXAMPLE 3

N,N-Bis(2-methoxymethyl)-3-(4-methoxyphenyl)-1,2,4-triazolo[3,4-a]phthalazin-6-methanamine hydrochloride A mixture of 6-(chloromethyl)-3-(4-methoxyphenyl)-1,2,4-triazolo[3,4-a]phthalazine (see Example 1, step C; 4 g) and bis-N-(2-methoxyethyl)amine (40 ml) is heated to about 140° C. for 30 h. The solvent is then evaporated under reduced pressure, the residue is disaggregated in water and extracted with methylene chloride. The separated organic phase is distilled under reduced pressure and the obtained oily residue is purified by silicagel column chromatography eluting with 0.5% methanol in chloroform. The solvent of the fractions containing the desired product (head fractions) is distilled under reduced pressure giving an oily residue which is salified with hydrogen chloride to give N,N-Bis(2-methoxymethyl)-3-(4-methoxyphenyl)-1,2,4-triazolo[3,4-a]phthalazin-6-methanamine hydrochloride (3.6 g) which crystallizes from ethanol/ethyl ether. M.p. 204°–206° C.

N.M.R. and I.R. spectra are in agreement with the assigned structure.

EXAMPLE 4

N,N-Bis-(2-methoxyethyl)-3-(4-methoxyphenyl)-1,2,4-triazolo[3,4-a]phthalazin-6-ethaneamine hydrochloride (A) 3-(4-Methoxyphenyl)-1,2,4-triazolo[3,4-a]-phthalazin-6-acetonitrile (0.65 g) is suspended in absolute ethanol (10 ml) and the cooled mixture is saturated with hydrogen chloride, heated at reflux for about 8 h and concentrated to dryness. The residue is taken up with water (5 ml) and brought to pH 7.5 with sodium bicarbonate. The mixture is filtered and the recovered solid is crystallized with ethanol/chloroform yielding 3-(4-methoxyphenyl)-1,2,4-triazolo[3,4-a]phthalazin-6-acetic acid ethyl ester (0.55 g). M.p. 201°–202° C.

(B) A portion of the above compound (0.3 g) is added to a solution of LiBH$_4$ (0.05 g) in anhydrous diglyme (5 ml) and the mixture is heated at 90° C. for 8 h. Then it is cooled to room temperature, acidified with acetic acid and concentrated to dryness. The residue is washed with water and crystallized from methylcellosolve, yielding 3-(4-methoxyphenyl)-1,2,4-triazolo[3,4-a]phthalazin-6-ethan-2-ol (0.17 g). M.p. 240°–243° C.

(C) 3-(4-Methoxyphenyl)-1,2,4-triazolo[3,4-a]-phthalazin-6-acetic acid ethyl ester (0.10 g) and triethylamine (0.4 g) are dissolved in methylene chloride (15 ml) and methanesulfonyl chloride (0.4 g) is added thereto. The reaction mixture is heated (water bath) for 1.5 h and then poured into ice-water (150 ml) and stirred until when an oily product separates from the mixture. This oily product solidifies and is then recovered by filtration, washed with cold diluted hydrochloric acid, then with diluted aqueous sodium hydroxide and finally with water up to neutrality. This residue is crystallized from methanol yielding 0.7 g of 3-(4-methoxyphenyl)-1,2,4-triazolo[3,4-a]phthalazin-6-ethan-2-ol, methanesulfonate.

(D) Essentially following the procedure of Example 3 but substituting the above obtained 3-(4-methoxyphenyl)-1,2,4-triazolo[3,4-a]phthalazin-6-ethan-2-ol, methanesulfonate, for 6-(chlorometil)-3-(4-methoxyphenyl)-1,2,4-triazolo[3,4-a]phthalazine, the product of the title, (i.e. N,N-Bis-(2-methoxyethyl)-3-(4-methoxyphenyl)-1,2,4-triazolo[3,4-a]phthalazin-6-ethaneamine hydrochloride) is obtained (yield 43%).

By essentially following the procedures of the above examples, the following compounds of formula I are obtained:

| Ex. No. | R | n | $R_1$ | $R_2$ | $R_3$ |
|---|---|---|---|---|---|
| 5 | 4-methoxyphenyl | 1 | piperidino | H | H |
| 6 | 4-methoxyphenyl | 1 | pyrrolidino | 7-$OCH_3$ | 8-$OCH_3$ |
| 7 | phenyl | 1 | $-OCH_2CH_2OCH_3$ | H | H |
| 8 | phenyl | 1 | $-OCH_2CH_2OCH_2CH_3$ | H | H |
| 9 | 4-methoxyphenyl | 1 | morpholino | H | H |
| 10 | 3,4,5-trimethoxyphenyl | 1 | $-N(CH_2CH_2OCH_3)_2$ | H | H |
| 11 | 2,5-dimethylphenyl | 1 | morpholino | H | H |
| 12 | 4-fluorophenyl | 1 | morpholino | H | H |
| 13 | 2,3-dimethylphenyl | 1 | 4-methylpiperazino | H | H |
| 14 | 4-methoxyphenyl | 2 | pyrrolidino | 7-$OCH_3$ | H |

-continued

| Ex. No. | R | n | R₁ | R₂ | R₃ |
|---|---|---|---|---|---|
| 15 | 2,3-dimethoxyphenyl (OCH₃, OCH₃) | 2 | pyrrolidin-1-yl (—N⟨ ⟩) | H | H |
| 16 | 4-methoxyphenyl (OCH₃) | 2 | pyrrolidin-1-yl (—N⟨ ⟩) | H | H |
| 17 | 4-methoxyphenyl (OCH₃) | 2 | $-N(CH_2CH_2OCH_3)_2$ | H | H |
| 18 | 4-(dimethylamino)phenyl (N(CH₃)₂) | 1 | pyrrolidin-1-yl (—N⟨ ⟩) | 8-OCH₃ | H |
| 19 | 2-methyl-4-(dimethylamino)phenyl (CH₃, N(CH₃)₂) | 1 | pyrrolidin-1-yl (—N⟨ ⟩) | H | H |
| 20 | 4-methoxyphenyl (OCH₃) | 1 | —N⟨ ⟩N—C₆H₅ | H | H |
| 21 | 3,4-dimethoxyphenyl (OCH₃, OCH₃) | 1 | pyrrolidin-1-yl (—N⟨ ⟩) | 9-OCH₃ | H |
| 22 | 3-chlorophenyl (Cl) | 1 | $-N(CH_2CH_2OCH_3)_2$ | H | H |
| 23 | 3,4-dimethylphenyl (CH₃, CH₃) | 1 | $-N(CH_3)_2$ | H | H |
| 24 | 3,4-dimethylphenyl (CH₃, CH₃) | 2 | $-OCH_2CH_3$ | H | H |
| 25 | 4-methoxyphenyl (OCH₃) | 2 | $-O-CH_2CH_3$ | 8-Cl | H |
| 26 | 4-methoxyphenyl (OCH₃) | 2 | $-N(CH_2CH_3)_2$ | 9-Cl | H |

-continued

| Ex. No. | R | n | $R_1$ | $R_2$ | $R_3$ |
|---|---|---|---|---|---|
| 27 | 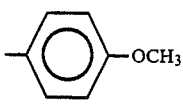 —⟨○⟩—OCH$_3$ | 2 | —N(CH$_2$CH$_2$OCH$_3$)$_2$ | 9-CH$_3$ | H |
| 28 | —⟨○⟩ | 2 | 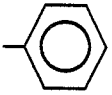 —N⟨ ⟩ | H | H |
| 29 | —⟨○⟩—OCH$_3$ | 1 |  —N⟨ ⟩—COOC$_2$H$_5$ | H | H |
| 30 | —⟨○⟩ | 1 | —N(CH$_2$CH$_3$)$_2$ | H | H |
| 31 | —⟨○⟩ | 2 | 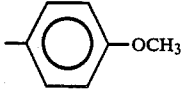 —N⟨ ⟩O | H | H |
| 32 | —⟨○⟩(OCH$_3$)(OCH$_3$) | 2 | —OCH$_2$CH$_2$OCH$_3$ | H | H |
| 33 | —⟨○⟩—OCH$_3$ | 1 | —N(CH$_3$)CH$_2$CH$_3$ | H | H |
| 34 | —⟨○⟩—N(CH$_3$)$_2$ | 2 | —N(CH$_3$)$_2$ | H | H |
| 35 | —⟨○⟩(CH$_3$)(N(CH$_3$)$_2$) | 2 | 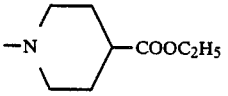 —N⟨ ⟩ | H | H |

PREPARATION OF THE STARTING MATERIALS

Preparation of 3-(4-methoxyphenyl)-1,2,4-triazolo[3,4-a]phthalazin-6-carbonitrile (A) 50% NaH (6 g) is suspended in 300 ml of anhydrous dimethylformamide in a 1 l flask and stirred for about 10 min, then, after cooling to 10° C., ethanethiol (9 ml) dissolved in anhydrous dimethylformamide (60 ml) is added thereto. The reaction mixture is stirred for about 30 min and then 38.6 g of 6-chloro-3-(4-methoxyphenyl)triazolo[3,4-a]phthalazine is added portionwise. The resulting mixture is stirred for about 5 h at 50° C. and cooled, a solid is collected by filtration, giving 30 g of 6-ethylthio-3-(4-methoxyphenyl)-1,2,4-triazolo[3,4-a]phthalazine.

By evaporating the solvent of the mother liquors, a solid is obtained which is taken up with water and collected by filtration giving a further crop of 7 g of 6-ethylthio-3-(4-methoxyphenyl)-1,2,4-triazolo[3,4-a]phthalazine. These two portions are pooled and crystallized from a mixture methanol/ethyl ester, 1:1 giving 36 g of pure product. M.p. 176°–178° C.

(a) 35.5 g of the above product are suspended in 450 ml of glacial acetic acid and 36% (v/v) hydrogen peroxide (37 ml). After 5 days of reaction, with stirring from time to time, the reaction mixture is poured into water (1500 ml) and the precipitate which forms is recovered by filtration yielding 3-(4-methoxyphenyl)-6-(ethylsulfony)-1,2,4-triazolo[3,4-a]phthalazine (35 g). M.p. 210°–213° C.

(C) This product is in turn dissolved in hot dimethylformamide (400 ml), the resulting solution is cooled to about 30° C. and potassium cyanide (11.5 g) is added thereto. This mixture is stirred at room temperature for about 5 h and then the solvent is distilled under reduced pressure. The residue is taken up with a small amount of water and crystallized from ethanol/chloroform yielding 26 g of 3-(4-methoxyphenyl)-1,2,4-triazolo[3,4-a]phthalazin-6-carbonitrile. M.p. 230°–232° C.

6-Chloro-3-(4-methoxyphenyl)-triazolo[3,4-a]phthalazine is described in European Patent Application No. 83100232.4.

Preparation of 3-(4-methoxyphenyl)-1,2,4-triazolo[3,4-a]phthalazin-6-acetonitrile (A) 3,4-dihydro-4-oxo-1-phthalazin-acetonitrile (126 g) is suspended in anhydrous pyridine (1300 ml) under anhydrous conditions. $P_2S_5$ (230 g) is added portionwise to this suspension at room temperature and with stirring, then the mixture is slowly heated to reflux temperature and kept at this temperature for about 2 h. Pyridine is then evaporated under reduced pressure and the residue is poured into water (3 l). The solid which separates is recovered by filtration, thoroughly wshed first with water and then with cold dilutes aqueous ammonia. The recovered solid is oven-dried, yielding 4-mercapto-phthalazin-acetonitrile (110 g).

(B) The above product (1 g) is added to a solution of hydrazine hydrate (1 g) in dioxane (15 ml) at 50° C. The mixture is heated at the reflux for 1 h and activated carbon is added. The solution which residuates after filtering the reaction mixture is concentrated to dryness, the obtained solid mass is taken up with water, recovered by filtration and crystallized from ethanol/chloroform yielding 0.91 g of 4-hydrazino-1-phthalazin-acetonitrile. M.p. 187°–190° C.

(C) A mixture of 4-hydrazino-1-phthalazin-acetonitrile (0.7 g), triethylamine (0.4 g), p-methoxybenzoyl-chloride (0.68 g), dioxane (10 ml), is heated at reflux for 5 h, then it is cooled, the solvent is evaporated under reduced pressure, the residue is taken up with water, recovered by filtration and crystallized from ethanol/chloroform, yielding 3-(4-methoxyphenyl)-1,2,4-triazolo[3,4-a]phthalazin-6-acetonitrile. M.p. 252°–254° C.

The starting 3,4-dihydro-4-oxo-phthalazin-acetonitrile is prepared from phthalyl anhydride according to the following method: finely powdered phthalyl anhydride (400 ml), cyanoacetic acid (260 g), anhydrous pyridine (360 ml) are heated at 60°–70° C. with stirring for 6 h. The reaction mass is left aside overnight, and then taken up with diluted aqueous hydrochloric acid (1 l) cold stirred for 30 min and filtered. The recovered solid is washed with water and crystallized from acetic acid. Then it is suspended in ethanol (1.4 l), hydrazine hydrate (60 ml) is slowly added and the resulting clear solution is heated at reflux for about 4 h. Then, the reaction mixture is allowed to cool to room temperature and the solid precipitate which forms is separated and washed with methanol, yielding 160 g of 3,4-dihydro-4-oxo-1-phthalazin-acetonitrile. M.p. 238°–240° C. (from ethanol/chloroform).

We claim:

1. A 1,2,4-triazolo[3,4-a]phthalazine of formula

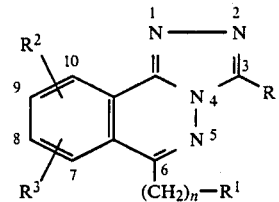

wherein

R represents phenyl or substituted phenyl wherein the phenyl ring is substituted with one, two or three substituents independently selected from $(C_1-C_4)$alkyl, $(C_1-C_4)$alkoxy, halogen, phenyl, hydroxy, amino, mono- and di-$(C_1-C_4)$alkylamino, $(C_2-C_4)$alkanoylamino and trifluoromethyl; n is 1 or 2;

$R^1$ is selected from an amino group of formula $NR^4R^5$ wherein $R^4$ and $R^5$, each independently, represents hydrogen, $(C_1-C_4)$alkyl, $(C_2-C_4)$alkenyl, $(C_1-C_4)$alkyl substituted with one or two groups independently selected from hydroxy, $(C_1-C_4)$alkoxy, halogen, carboxy and $(C_1-C_4)$alkoxycarbonyl; a $(C_1-C_4)$alkyl or unsubstituted phenyl-$(C_1-C_4)$alkyl group wherein the alkyl portion may be substituted as defined above and the phenyl portion may be substituted with 1, 2 or 3 substituents selected from $(C_1-C_4)$alkyl, $(C_1-C_4)$alkoxy, halogen, phenyl, hydroxy, amino, mono- and di-$(C_1-C_4)$alkylamino, $(C_1-C_4)$alkanoylamino, and trifluoromethyl, or $R^4$ and $R^5$ taken together with the adjacent nitrogen atom may represent a saturated 4, 5, 6 or 7-membered heterocyclic ring which may have one additional heteroatom selected from nitrogen, oxygen and sulfur and optionally bear one or two substituents independently selected from $(C_1-C_4)$alkyl, phenyl, substituted phenyl, hydroxy, and carbo-$(C_1-C_4)$alkoxy, or $R^1$ represents an alkoxy or cycloalkoxy group of formula $-OR^6$ wherein $R^6$ stands for a $(C_1-C_6)$alkyl group substituted with one or two groups independently selected from hydroxy, amino, mono- or di-$(C_1-C_4)$alkylamino, $(C_1-C_4)$alkoxy, halogen, oxo, carboxy, and $(C_1-C_4)$alkoxycarbonyl, or $R^6$ is a $(C_5-C_8)$cycloalkyl group optionally substituted with one or more hydroxy or $(C_1-C_4)$alkoxy groups and $R^2$ and $R^3$, each independently, represents hydrogen, halogen, $(C_1-C_4)$alkyl or $(C_1-C_4)$alkoxy, and the pharmaceutically acceptable acid-addition salt thereof.

2. A compound according to claim 1 wherein R is phenyl or subtituted phenyl, and $R^1$ is an amine of formula $NR^4R^5$, wherein $R^4$ and $R^5$ are as defined above.

3. A compound according to claim 1 wherein R is phenyl and $R^1$ is $NR^4R^5$ wherein $R^4$ and $R^5$ represent $(C_1-C_4)$alkyl groups or $(C_1-C_4)$alkyl groups substitued as defined above or $R^4$ and $R^5$ taken together with the adjacent nitrogen atom represent a pyrrolidino, pyrazolidino, piperidino, imidazolidino and morpholino group.

4. A compound according to claim 1 which is 6-[(2-methoxyethoxy)methyl]-3-(4-methoxyphenyl)-1,2,4-triazolo[3,4-a]phthalazine.

5. An intermediate compound in the process for preparing a compound of claim 1 which has one of the following formulas

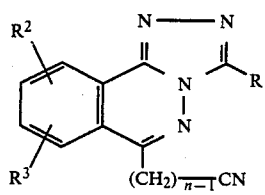

II

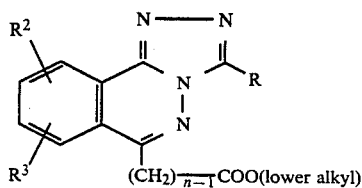

III

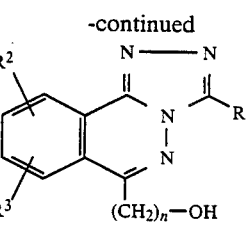

IV

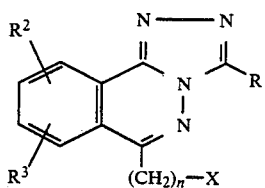

V wherein n is 1 or 2, R, $R^2$ and $R^3$ are as defined in claim 1 and X is a "good leaving group" selected from chlorine, bromine or iodine atoms and sulfonic acid ester groups.

6. An anti-anxiety, pharmaceutical formulation which comprises a compound of claim 1 as the active ingredient in admixture with a pharmaceutically acceptable vehicle.

7. A method of treating anxiety in a patient in need thereof which comprises administering to the patient an effective amount of a 1,2,4-triazolo[3,4-a]phthalazine of claim 1.

* * * * *

UNITED STATES PATENT AND TRADEMARK OFFICE
CERTIFICATE OF CORRECTION

PATENT NO. : 4,783,461

DATED : November 8, 1988

INVENTOR(S) : Emilio Occelli et al.

It is certified that error appears in the above-identified patent and that said Letters Patent is hereby corrected as shown below:

At column 2, line 59, the patent reads "activity in" and should read --activity on--.

At column 4, line 35, the patent reads "NaBH, or LiBH," and should read --$NaBH_4$ or $LiBH_4$--.

At column 4, line 37, the patent reads "such as LiAlH," and should read --such as LiAlH4,--.

At column 5, line 16, the patent reads "triazolo-pthalazine" and should read --triazolo-phthalazine--.

At column 5, line 64, the patent reads "for water" and should read --of water--.

At column 8, line 20, the patent rads "(2-methoxymethyl)" and should read --(2-methoxyethyl)--.

At column 14, line 59, the patent reads "(a) 35.5 g" and should read --(B) 35.5 g--.

At column 14, line 64, the patent reads "(ethylsulfony)" and should read --(ethylsulfonyl)--.

At column 15, line 26, the patent reads "dilutes" and should read --diluted--.

At column 15, line 27, the patent reads "mercapto-phthalazin" and should read --mercapto-1-phthalazin--.

UNITED STATES PATENT AND TRADEMARK OFFICE
CERTIFICATE OF CORRECTION

PATENT NO. : 4,783,461

DATED : November 8, 1988

INVENTOR(S) : Emilio Occelli et al.

It is certified that error appears in the above-identified patent and that said Letters Patent is hereby corrected as shown below:

At column 15, line 49, the patent reads "4-oxo-phthalazin" and should read --4-oxo-1-phthalazin--.

At column 16, line 26, the patent reads "unsubstituted" and should read --substituted--..

At column 16, line 56, the patent reads "subtituted" and should read --substituted--

At column 16, line 61, the patent reads "substitued" and should read --substituted--.

On the cover page, in the Abstract at the second last line, the patent reads "are as active as" and should read --are active as--.

Signed and Sealed this

Twenty-seventh Day of June, 1989

*Attest:*

DONALD J. QUIGG

*Attesting Officer*  *Commissioner of Patents and Trademarks*